United States Patent
Furudate et al.

(10) Patent No.: US 10,413,214 B2
(45) Date of Patent: Sep. 17, 2019

(54) MAGNETIC RESONANCE IMAGING APPARATUS AND CONSOLE DEVICE THEREOF

(71) Applicant: TOSHIBA MEDICAL SYSTEMS CORPORATION, Otawara-shi (JP)

(72) Inventors: Naoyuki Furudate, Tochigi (JP); Sayo Syukuri, Fukuoka (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 464 days.

(21) Appl. No.: 14/628,779

(22) Filed: Feb. 23, 2015

(65) Prior Publication Data
US 2015/0164367 A1  Jun. 18, 2015

Related U.S. Application Data

(63) Continuation of application No. PCT/JP2013/072322, filed on Aug. 21, 2013.

(30) Foreign Application Priority Data

Aug. 24, 2012 (JP) .................................. 2012-185353

(51) Int. Cl.
*A61B 5/055* (2006.01)
*G01R 33/54* (2006.01)
*A61B 5/00* (2006.01)

(52) U.S. Cl.
CPC .............. *A61B 5/055* (2013.01); *A61B 5/742* (2013.01); *A61B 5/7475* (2013.01); *G01R 33/543* (2013.01); *G01R 33/546* (2013.01)

(58) Field of Classification Search
CPC .... G01R 33/54; G01R 33/546; G01R 33/543; A61B 5/055; A61B 5/742; A61B 5/7475
See application file for complete search history.

(56) References Cited

U.S. PATENT DOCUMENTS

| | | | | |
|---|---|---|---|---|
| 6,144,201 A | * | 11/2000 | Miyazaki | G01R 33/5673 324/306 |
| 8,217,648 B2 | | 7/2012 | Kachi et al. | |
| 8,476,903 B2 | | 7/2013 | Furudate | |
| 2010/0092056 A1 | * | 4/2010 | Rofsky | G01R 33/54 382/131 |

(Continued)

FOREIGN PATENT DOCUMENTS

| | | |
|---|---|---|
| JP | 2006-167345 | 6/2006 |
| JP | 2008-001632 | 1/2008 |

(Continued)

OTHER PUBLICATIONS

Office Action dated Dec. 13, 2016 in JP 2012-185353.

(Continued)

*Primary Examiner* — Elmer M Chao
(74) *Attorney, Agent, or Firm* — Nixon & Vanderhye P.C.

(57) ABSTRACT

A magnetic resonance imaging apparatus includes a processor and a memory. The memory stores processor-executable instructions that, when executed by the processor, cause the processor to receive a breath holdable time of a subject and adjust a parameter value of an imaging parameter included in imaging condition for imaging of the subject, according to the breath holdable time.

13 Claims, 17 Drawing Sheets

(56) References Cited

U.S. PATENT DOCUMENTS

| | | | | |
|---|---|---|---|---|
| 2010/0145182 A1* | 6/2010 | Schmidt | ............... | G01R 33/546 600/410 |
| 2011/0181286 A1* | 7/2011 | Kamada | ................. | A61B 5/055 324/309 |
| 2012/0218123 A1* | 8/2012 | Ji | ......................... | A61B 5/7232 340/870.07 |

FOREIGN PATENT DOCUMENTS

| | | |
|---|---|---|
| JP | 2009-101133 A | 5/2009 |
| JP | 2009-160273 A | 7/2009 |
| JP | 2011-161212 A | 8/2011 |
| JP | 2011-177399 | 9/2011 |
| JP | 2012-75509 | 4/2012 |
| JP | 2013-009722 | 1/2013 |
| JP | 2013-138808 | 7/2013 |

OTHER PUBLICATIONS

"MAGNETON Skyra 3T/MAGNETON Aera 1.5T Near future platform 3T/1.5T MRI which operates at full swing in the special hospital which bears the center of pediatric care", [online], Oct. 2011, [Dec. 2, 2016 search], Internet <URL:. http://www.innervision.co.jp/suite/siemens/supplement/1110/index.html>, and URL:http://www.innervision.co.jp/suite/siemens/supplement/1110/cr01/index.html> with partial English translation.

International Search Report for PCT/JP2013/072322, dated Oct. 1, 2013, 6 pages.

Written Opinion of the International Searching Authority (non-English language), dated Oct. 1, 2013, 5 pages.

\* cited by examiner

FIG.3

| BREATH HOLDABLE TIME | SLICE THICKNESS | NUMBER OF SLICES | PE MATRIX | RO MATRIX | SPEEDER RATIO |
|---|---|---|---|---|---|
| 20 | 0.003 | 60 | 160 | 320 | 2.4 |
| 15 | 0.004 | 45 | 170 | 320 | 2.5 |
| 10 | 0.005 | 36 | 140 | 320 | 2.5 |
| 7 | 0.007 | 25 | 140 | 320 | 2.5 |

FIG.7

| TR | NUMBER OF SLICES | SLICE THICKNESS [mm] |
|---|---|---|
| Min 24.5  ◄► (31a) | 25 ◄► (31b) | 7 ◄► (31c) ▶ |
| MATRIX PE/RO | FIELD OF VIEW PE/RO [cm] | SPEEDER |
| 31d~ 140 ◄► 320 ◄► (31e) | 31f~ 33 ◄► 35 ◄► (31g) | PE (2.5) ▶ (31h) |

TIME CHART (33)
33a 33b 33c

Dynamic Plan

| CONTRAST AGENT A (32a) | CONTRAST AGENT B (32b) |
| ADRENAL GLANDS (32c) | KIDNEYS (32d) |
| TDC (32e) | |

Breath Hold

| 34a | 34b | 34c | 34d |
|---|---|---|---|
| 20 sec<br>Thk: 3 mm<br>NS: 60<br>Mtx: 160x320<br>SPDR: 2.4 | 15 sec<br>Thk: 4 mm<br>NS: 45<br>Mtx: 170x320<br>SPDR: 2.5 | 10 sec<br>Thk: 5 mm<br>NS: 36<br>Mtx: 140x320<br>SPDR: 2.5 | 7 sec<br>Thk: 7 mm<br>NS: 25<br>Mtx: 140x320<br>SPDR: 2.5 |

| IMAGING REGION | BREATH HOLDABLE TIME | SLICE THICKNESS | NUMBER OF SLICES | PE MATRIX | RO MATRIX | SPEEDER RATIO |
|---|---|---|---|---|---|---|
| LIVER 23 cm | 7 | 0.008 | 28 | 122 | 320 | 2.8 |
| | 10 | 0.007 | 32 | 138 | 320 | 2.3 |
| | 15 | 0.005 | 46 | 144 | 320 | 2.2 |
| | 20 | 0.005 | 46 | 188 | 320 | 2 |
| LIVER 18 cm | 7 | 0.007 | 25 | 132 | 320 | 2.4 |
| | 10 | 0.007 | 25 | 172 | 320 | 2 |
| | 15 | 0.005 | 36 | 184 | 320 | 2 |
| | 20 | 0.005 | 36 | 214 | 320 | 1.7 |
| PANCREAS/ GALLBLADDER | 7 | 0.005 | 26 | 128 | 320 | 2.4 |
| | 10 | 0.004 | 37 | 132 | 320 | 2.4 |
| | 15 | 0.003 | 50 | 134 | 320 | 2.3 |
| ADRENAL GLANDS | 10 | 0.003 | 33 | 132 | 288 | 2.2 |
| | 15 | 0.002 | 50 | 132 | 288 | 2.2 |
| KIDNEYS | 10 | 0.005 | 36 | 134 | 320 | 2.4 |
| | 15 | 0.004 | 45 | 156 | 320 | 2.3 |

FIG.15

| MATRIX PE/RO | | NUMBER OF SLICES/SLICE THICKNESS [mm] | | SPEEDER | |
|---|---|---|---|---|---|
| 31d<br>132 ◁▷ | 31e<br>320 ◁▷ | 31b<br>25 ◁▷ | 31c<br>7 ◁▷ | | 31h<br>PE (2.4) ▷ |

130

TIME CHART 33b  33b  33  33b

| LIVER<br>23 cm | LIVER<br>18 cm | PANCREAS/<br>GALLBLADDER | ADRENAL<br>GLANDS | KIDNEYS |
|---|---|---|---|---|

Breath Hold

| 135a | 135b | 135c | 135d |
|---|---|---|---|
| 7 sec<br>Thk: 7 mm<br>NS: 25<br>Mtx: 132x320<br>SPDR: 2.4 | 10 sec<br>Thk: 7 mm<br>NS: 25<br>Mtx: 172x320<br>SPDR: 2 | 15 sec<br>Thk: 5 mm<br>NS: 36<br>Mtx: 184x320<br>SPDR: 2 | 20 sec<br>Thk: 5 mm<br>NS: 36<br>Mtx: 214x320<br>SPDR: 1.7 |

135

Dynamic Plan

135e — Single-arterial Phase
135f — Dual-arterial Phase
135g — TDC
135h — Pre-dynamic

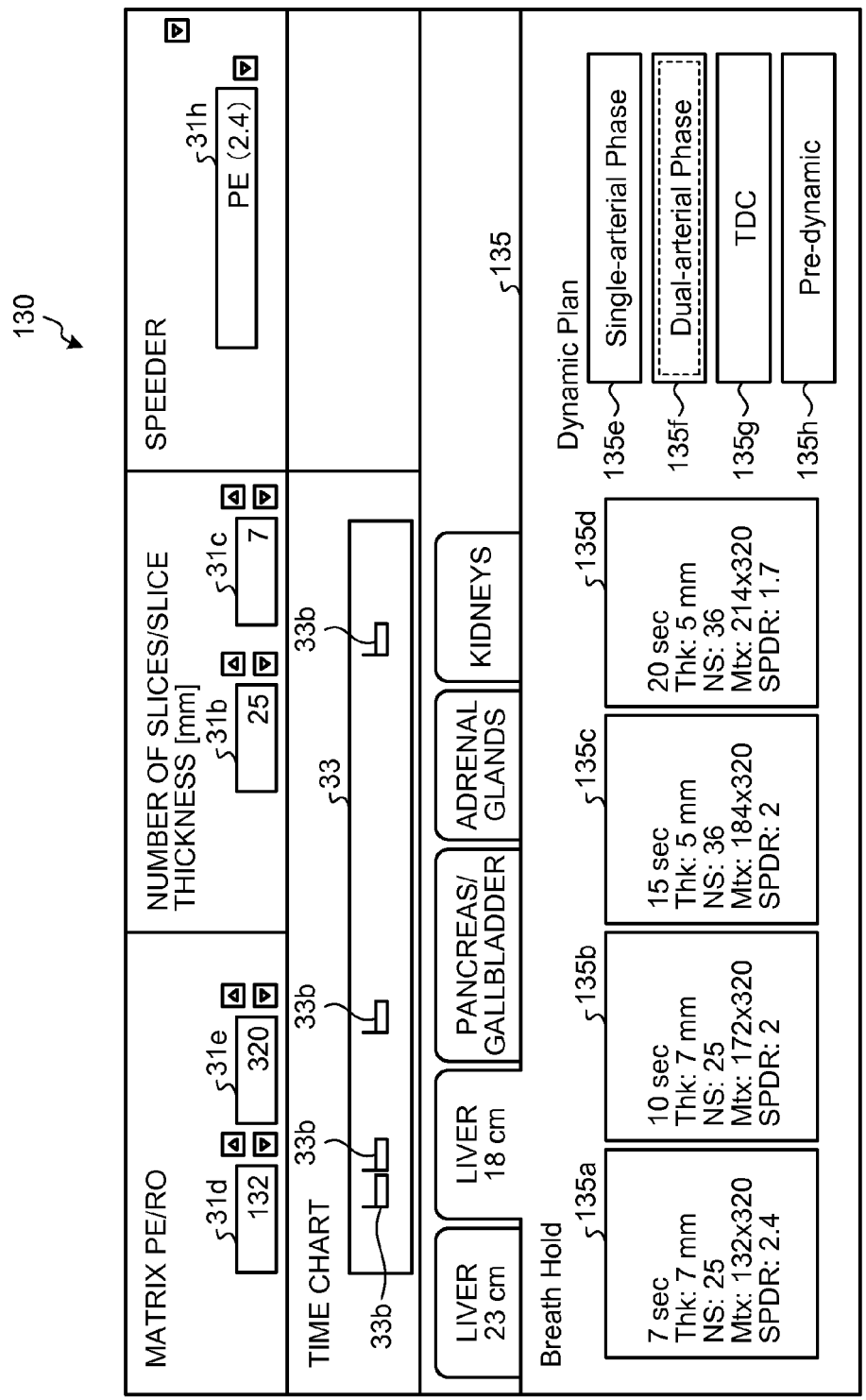

| MATRIX PE/RO | NUMBER OF SLICES/SLICE THICKNESS [mm] | SPEEDER |
|---|---|---|
| 31d<br>132 ◄ ► | 31b<br>25 ◄ ►  31c<br>7 ◄ ► | ▶ |
| 31e<br>320 ◄ ► | | 31h<br>PE (2.4) ▶ |

TIME CHART

33b ─ 33b   33b   33b   33b ─ 33  
　　　　　　　　　　　　　　　　⌐

| LIVER<br>23 cm | LIVER<br>18 cm | PANCREAS/<br>GALLBLADDER | ADRENAL<br>GLANDS | KIDNEYS |
|---|---|---|---|---|
| Breath Hold ⌒135a | ⌒135b | | ⌒135c | ⌒135d |
| 7 sec<br>Thk: 7 mm<br>NS: 25<br>Mtx: 132x320<br>SPDR: 2.4 | 10 sec<br>Thk: 7 mm<br>NS: 25<br>Mtx: 172x320<br>SPDR: 2 | 15 sec<br>Thk: 5 mm<br>NS: 36<br>Mtx: 184x320<br>SPDR: 2 | | 20 sec<br>Thk: 5 mm<br>NS: 36<br>Mtx: 214x320<br>SPDR: 1.7 |

135

Dynamic Plan
- 135e — Single-arterial Phase
- 135f — Dual-arterial Phase
- 135g — TDC
- 135h — Pre-dynamic

MAGNETIC RESONANCE IMAGING APPARATUS AND CONSOLE DEVICE THEREOF

CROSS-REFERENCE TO RELATED APPLICATIONS

This application is a continuation of PCT international application Ser. PCT/JP2013/072322 filed on Aug. 21, 2013 which designates the United States, and which claims the benefit of priority from Japanese Patent Application No. 2012-185353, filed on Aug. 24, 2012; the entire contents of which are incorporated herein by reference.

FIELD

Embodiments described herein relate generally to a magnetic resonance imaging apparatus and a console device thereof.

BACKGROUND

Conventional, as a technique related to a magnetic resonance imaging apparatus, there is a technique that enables to store protocols in which imaging conditions are preset with respect to clinical purposes, to read appropriate one of the protocols according to a purpose and to execute imaging of a subject. In this type of technique, the preset imaging conditions are limited and thus an operator appropriately adjusts the imaging conditions according to a state of the subject. As a result, image qualities of obtained images may differ depending on knowledge and skills of the operator.

BRIEF DESCRIPTION OF THE DRAWINGS

FIG. 3 is an example of breath-hold setting information according to the first embodiment;
FIGS. 5 to 7 are explanatory diagrams of adjustment of parameter values performed by a parameter adjustment unit according to the first embodiment;
FIG. 9 is an example of breath-hold setting information according to a second embodiment;
FIGS. 15 to 17 are explanatory diagrams of time chart display performed by a time-chart-display controller according to the second embodiment.

DETAILED DESCRIPTION

A magnetic resonance imaging apparatus according to an embodiment includes a processor and a memory. The memory stores processor-executable instructions that, when executed by the processor, cause the processor to receive a breath holdable time of a subject; and adjust a parameter value of an imaging parameter included in imaging condition for imaging of the subject, according to the breath holdable time.

First Embodiment

Figure 1:
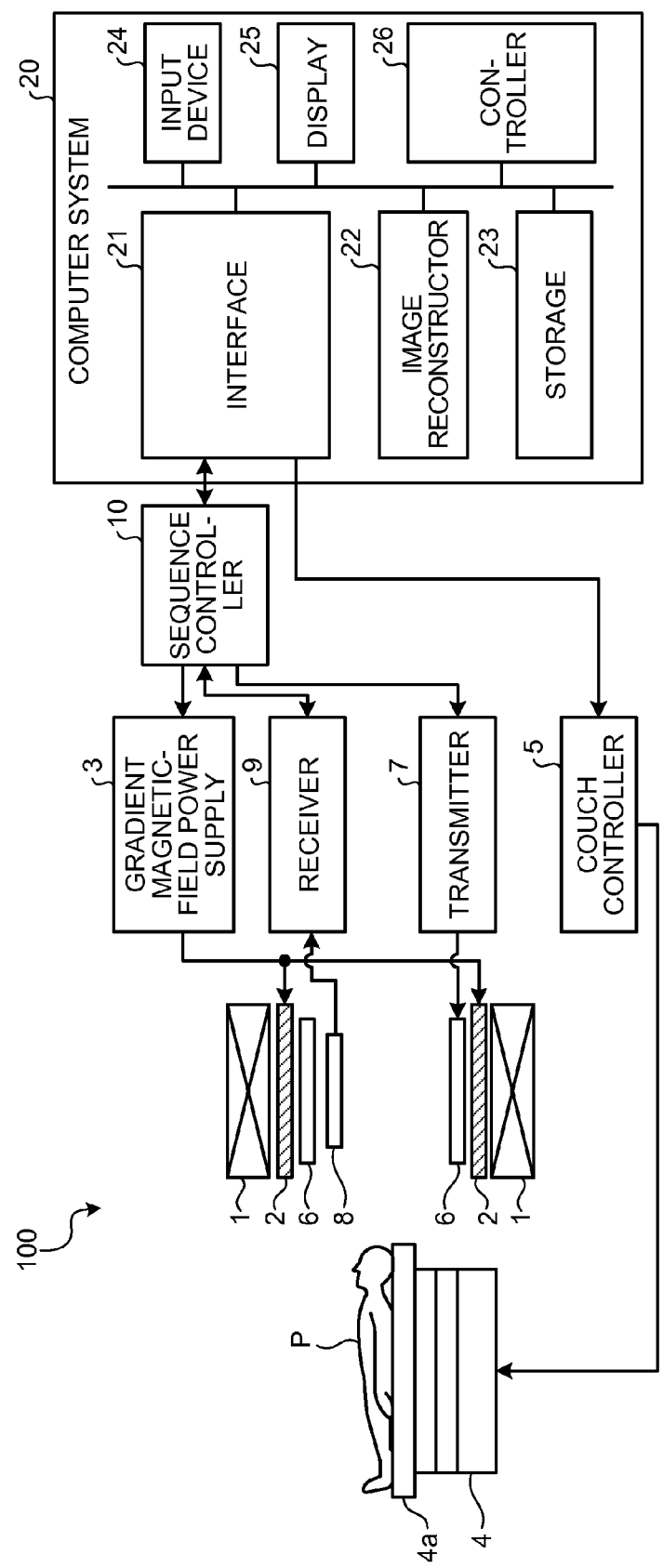
FIG. 1 depicts a configuration of an MRI apparatus according to a first embodiment.

FIG. 1 depicts a configuration of an MRI apparatus according to a first embodiment. As shown in FIG. 1, an MRI apparatus 100 according to the first embodiment includes a magnetostatic field magnet 1, a gradient coil 2, a gradient magnetic-field power supply 3, a couch 4, a couch controller 5, a transmitting RF (Radio Frequency) coil 6, a transmitter 7, a receiving RF coil 8, a receiver 9, a sequence controller 10, and a computer system 20.

The static magnetic field magnet 1 is formed in a hollow cylindrical shape and generates a uniform static magnetic field in the internal space. For example, a permanent magnet or a superconducting magnet may be used as the static magnetic field magnet 1.

The gradient coil 2 is formed in a hollow cylindrical shape and is placed within the static magnetic field magnet 1. The gradient coil 2 is formed by combining three coils corresponding to X, Y, and Z axes perpendicular to each other and these three coils individually receive current supply from the gradient magnetic-field power supply 3 explained later and generate gradient magnetic fields having magnetic field strengths that change along the X, Y, and Z axes, respectively. The direction of the Z axis is the same direction as that of the static magnetic field. The gradient magnetic-field power supply 3 supplies a current to the gradient coil 2.

The gradient magnetic fields along the X, Y, and Z axes generated by the gradient coil 2 correspond to, for example, a slice-select gradient magnetic field Gss, a phase-encode gradient magnetic field Gpe, and a read-out gradient magnetic field Gro, respectively. The slice-select gradient magnetic field Gss is used to optionally determine an imaging section. The phase-encode gradient magnetic field Gpe is used to change the phase of a magnetic resonance signal according to a spatial position. The read-out gradient magnetic field Gro is used to change the frequency of the magnetic resonance signal according to a spatial position.

The couch 4 includes a couchtop 4a on which a subject P is placed, and the couchtop 4a is inserted into a hollow (an imaging opening) of the gradient coil 2 under a control of the couch controller 5 explained later with the subject P being placed on the couchtop 4a. The couch 4 is usually installed in such a manner that the longitudinal direction thereof is parallel to the central axis of the static magnetic field magnet 1. The couch controller 5 is a device that controls the couch 4 under a control of a controller 26 and drives the couch 4 to move the couchtop 4a in the longitudinal direction and the vertical direction.

The transmitting RF coil 6 is placed within the gradient coil 2 and generates an RF (Radio Frequency) pulse (a high-frequency magnetic-field pulse) based on a high-frequency pulse current supplied from the transmitter 7. The transmitter 7 supplies a high-frequency pulse current corresponding to a Lamor frequency to the transmitting RF coil 6. The receiving RF coil 8 is placed within the gradient coil 2 and receives a magnetic resonance signal emitted from the subject P under an influence of the RF pulse. Upon receiving of the magnetic resonance signal, the receiving RF coil 8 outputs the magnetic resonance signal to the receiver 9.

The receiver 9 generates magnetic resonance (MR) signal data based on the magnetic resonance signal output from the receiving RF coil 8. The receiver 9 generates the MR signal data by digitally converting the magnetic resonance signal output from the receiving RF coil 8. The MR signal data is associated with information of spatial frequencies in a phase encode direction, a read out direction, and a slice encode direction by the slice-select gradient magnetic field Gss, the phase-encode gradient magnetic field Gpe, and the read-out gradient magnetic field Gro mentioned above and is arranged in a k-space. Upon generation of the MR signal data, the receiver 9 transmits the MR signal data to the sequence controller 10.

The sequence controller 10 performs scanning of the subject P by driving the gradient magnetic-field power supply 3, the transmitter 7, and the receiver 9 based on sequence execution data transmitted from the computer system 20. The sequence execution data in this case is information that defines a pulse sequence indicating a procedure for performing scanning of the subject P, such as a strength of power supplied from the gradient magnetic-field power supply 3 to the gradient coil 2, a timing of the supply of the power, a strength of the RF signal transmitted by the transmitter 7 to the transmitting RF coil 6, a timing of the transmission of the RF signal, and a timing of detection of the magnetic resonance signal by the receiver 9. When the MR signal data is transmitted from the receiver 9 after the gradient magnetic-field power supply 3, the transmitter 7, and the receiver 9 are driven based on the sequence execution data, the sequence controller 10 transfers the MR signal data to the computer system 20.

The computer system 20 executes the entire control of the MRI apparatus 100. For example, the computer system 20 drives the elements included in the MRI apparatus 100, thereby performing scanning of the subject P or image reconstruction. The computer system 20 includes an interface 21, an image reconstructor 22, a storage 23, an input device 24, a display 25, and the controller 26. That is, the computer system 20 functions as a console device of the MRI apparatus 100.

The interface 21 controls input and output of various signals transmitted to or received from the sequence controller 10. For example, the interface 21 transmits the sequence execution data to the sequence controller 10 and receives the MR signal data from the sequence controller 10. Upon receiving of the MR signal data, the interface 21 stores the MR signal data in the storage 23 with respect to each subject P.

The image reconstructor 22 performs post-processing, that is, a reconstruction process such as Fourier transformation of the MR signal data stored in the storage 23, thereby generating spectrum data or image data of a desired nuclear spin in the subject P.

The storage 23 stores therein various types of data and various programs necessary for processes performed by the controller 26 explained later. For example, the storage 23 stores therein the MR signal data received by the interface 21, the spectrum data or the image data generated by the image reconstructor 22, and the like, with respect to each subject P. The storage 23 is, for example, a semiconductor memory device such as a RAM (Random Access Memory), a ROM (Read Only Memory), or a flash memory, or a storage device such as a hard disk or an optical disk.

The input device 24 receives various instructions or information input from an operator. As the input device 24, a pointing device such as a mouse or a trackball, a selection device such as a mode selector switch, or an input device such as a keyboard can be appropriately used.

The display 25 displays various kinds of information such as the spectrum data or the image data under a control of the controller 26. A display device such as a liquid crystal display can be used as the display 25.

The controller 26 includes a processor such as a CPU (Central Processing Unit) and MPU (Micro processing unit), a memory, and the like (not shown) and executes the entire control of the MRI apparatus 100. The memory stores processor-executable instructions that, when executed by the processor, cause the processor to perform the processes described later as being performed by the units included in the controller 26. For example, the controller 26 generates various kinds of sequence execution data based on imaging conditions input by the operator via the input device 24 and transmits the generated sequence execution data to the sequence controller 10, thereby controlling scanning. When the MR signal data is transmitted from the sequence controller 10 as a result of scanning, the controller 26 controls the image reconstructor 22 to reconstruct an image based on the transmitted MR signal data.

The configuration of the MRI apparatus 100 according to the first embodiment is as explained above. With this configuration, the MRI apparatus 100 receives a time during which a subject can hold his/her breath (hereinafter, "breath holdable time") and adjusts imaging parameter values included in imaging conditions for imaging of the subject according to the received breath holdable time.

As a technique related to the MRI apparatus, there is a conventional technique that enables to store protocols in which imaging conditions are preset with respect to clinical purpose, to read appropriate one of the protocols according to a purpose, and to execute imaging of a subject. In this technique, the preset imaging conditions are limited and thus the operator appropriately adjusts the imaging conditions according to a state of the subject. For example, in the case of imaging accompanied by breath hold of a subject, breath holdable times differ according to patients. Particularly in the case of the elderly, the breath holdable times are short. In such cases, the preset imaging conditions are adjusted to adapt to the breath holdable times.

Generally, to shorten a time required for imaging, a TR (a repetition time) or the number of encodes needs to be reduced. However, the TR or the number of encodes has a trade-off relation with an SNR (Signal to Noise Ratio) or a resolution. The operator appropriately adjusts the imaging conditions based on knowledge about MRI. Accordingly, in the conventional technique mentioned above, image qualities of obtained images may differ according to knowledge and skills of the operator.

In contrast, with the MRI apparatus 100 according to the present embodiment, an operator can adjust the imaging parameters according to the breath holdable time, which is a simple index. Therefore, the imaging conditions can be appropriately set regardless of special knowledge of the operator. As a result, images with a uniform image quality independent of the operator can be obtained. The MRI apparatus 100 according to the present embodiment is explained below in more detail.

Figure 2:
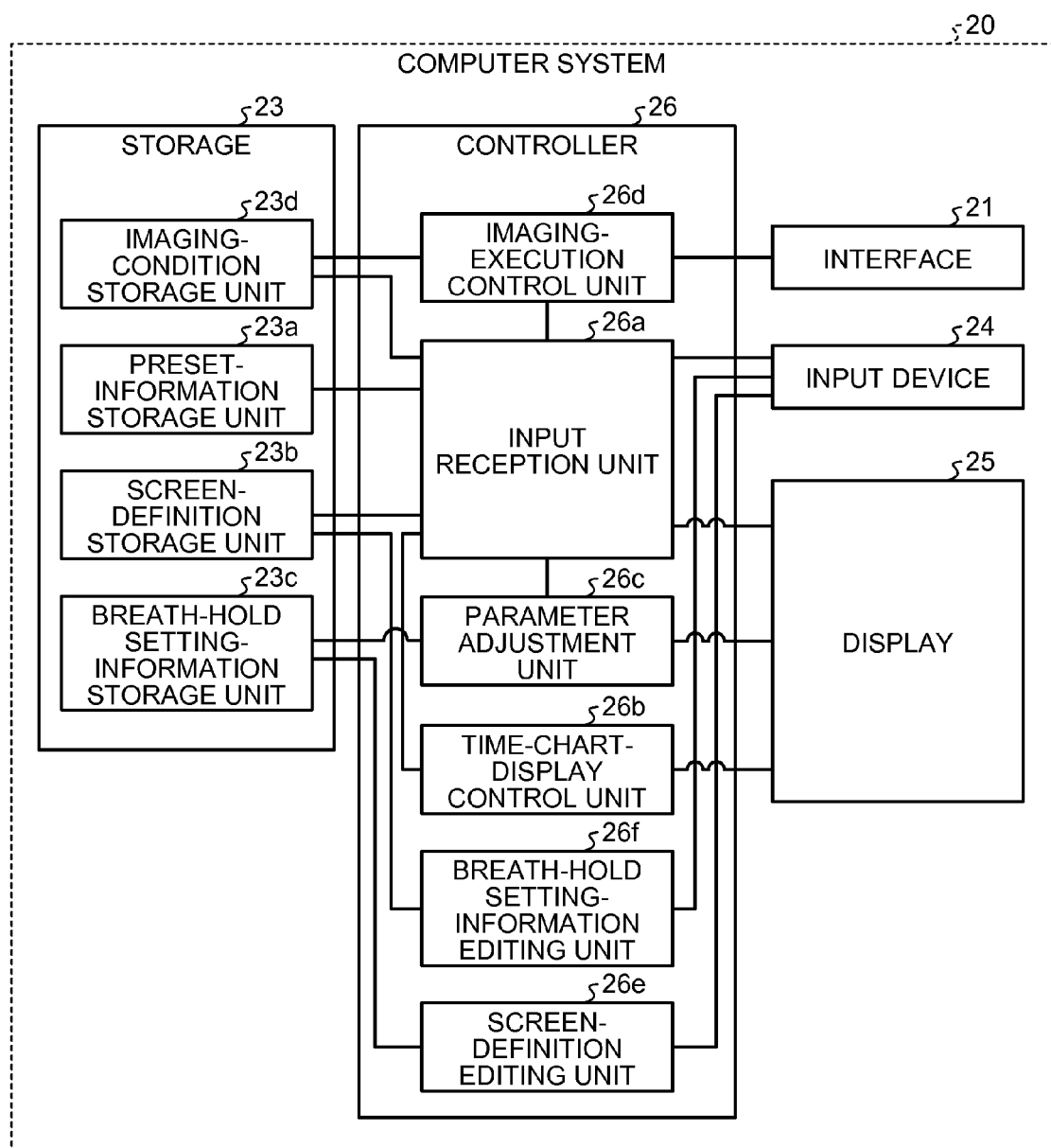
FIG. 2 is a block diagram of a detailed configuration of the MRI apparatus according to the first embodiment.

FIG. 2 is a block diagram of a detailed configuration of the MRI apparatus according to the first embodiment. FIG. 2 depicts the interface 21, the storage 23, the input device 24, the display 25, and the controller 26 among the units included in the computer system 20 shown in FIG. 1.

As shown in FIG. 2, the storage 23 stores a preset-information storage unit 23a, a screen-definition storage unit 23b, a breath-hold setting-information storage unit 23c, and an imaging-condition storage unit 23d.

The preset-information storage unit 23a stores therein preset information of parameter values of a plurality of imaging parameters which are preset as protocols with respect to each of imaging purposes and imaging methods. The imaging purposes in this case are, for example, "high contrast" and "high resolution". The imaging methods are "FASE (Fast Advanced Spin Echo)", "FSE (Fast Spin Echo)", "FE (Field Echo)", "SE (Spin Echo)", and the like. The imaging parameter are, for example, the TR, a TE (echo time), a size of a field of view (FOV), a slice thickness, the number of slices, a matrix, and a SPEEDER ratio. That is, the preset-information storage unit 23a therein stores plural imaging protocols including imaging conditions for imaging of a subject.

The screen-definition storage unit 23b stores therein screen definition information that defines forms of an imaging-condition editing screen for setting imaging conditions. For example, the screen definition information defines arrangement of constituent elements that constitute a GUI (Graphical User Interface) as the imaging-condition editing screen, such as labels, text boxes, and buttons, characters displayed on the buttons, and relations between the constituent elements and the imaging parameters. The screen-definition storage unit 23b stores therein the screen definition information as an external file that can receive editing of the screen definition information.

The breath-hold setting-information storage unit 23c stores therein breath-hold setting information, in which a plurality of breath holdable times are associated with parameter values of the imaging parameters that are set according to the breath holdable times, respectively. The breath-hold setting-information storage unit 23c stores therein the breath-holding setting information with respect to each of the protocols. In the present embodiment, the breath-hold setting-information storage unit 23c stores therein the breath-holding setting information as an external file that can receive editing of the breath-hold setting information.

FIG. 3 is an example of the breath-hold setting information according to the first embodiment. As shown in FIG. 3, the breath-hold setting information includes, for example, the breath holdable time (seconds), the slice thickness (m (meter)), the number of slices, a PE (Phase Encode) matrix, a RO (Read Out) matrix, and the SPEEDER ratio associated with each other. In this case, the PE matrix is the number of matrixes in the phase encode direction and the RO matrix is the number of matrixes in the read out direction.

As shown in FIG. 3, four times of "20 (seconds)", "15 (seconds)", "10 (seconds)", and "7 (seconds)" are set as the breath holdable time, for example. In this case, for example, it is set in the breath-hold setting information that a smaller slice thickness and a larger number of slices are adopted for a longer breath holdable time. This is because, when the same volume of data is to be collected at one time of breath hold, the number of encodes can be increased as the breath holdable time is longer, so that the number of slices that can be collected at one time of breath hold is increased and that the slice thickness of one slice is decreased. For example, as shown in FIG. 3, the slice thickness "0.003 (m)" and the number of slices "60" are associated with the breath holdable time "20 (seconds)", the slice thickness "0.004 (m)" and the number of slices "45" are associated with the breath holdable time "15 (seconds)", the slice thickness "0.005 (m)" and the number of slices "36" are associated with the breath holdable time "10 (seconds)", and the slice thickness "0.007 (m)" and the number of slices "25" are associated with the breath holdable time "7 (seconds)".

In this way, the parameter values are set in the breath-hold setting information in consideration of respective correlative relations between the imaging parameters and trade-off with the SNR or the resolution. While a case where the breath holdable time, the slice thickness, the number of slices, the PE matrix, the RO matrix, and the SPEEDER ratio are set in the breath-hold setting information has been explained above, examples of the breath-hold setting information are not limited thereto. For example, the TR or the TE can be set in addition to these imaging parameters.

Referring back to FIG. 2, the imaging-condition storage unit 23d stores therein imaging conditions for imaging of a subject. The imaging parameters that are set based on the preset information stored in the preset-information storage unit 23a and that are adjusted according to the breath holdable time are stored in the imaging-condition storage unit 23d as the imaging conditions.

As shown in FIG. 2, the controller 26 includes an input reception unit 26a, a time-chart-display control unit 26b, a parameter adjustment unit 26c, an imaging-execution control unit 26d, a screen-definition editing unit 26e, and a breath-hold setting-information editing unit 26f.

The input reception unit 26a receives various instructions or various kinds of information input by an operator via the input device 24 and performs processes according to the received instructions or information. For example, the input reception unit 26a receives a request for display of an imaging-condition editing screen, selection of a protocol, or an instruction to start imaging. The input reception unit 26a also receives parameter values related to the various imaging parameters via the imaging-condition editing screen. The input reception unit 26a receives the breath holdable time of a subject via the imaging-condition editing screen.

For example, when a request for display of the imaging-condition editing screen is received from an operator, the input reception unit 26a reads the screen definition information stored in the screen-definition storage unit 23b and outputs an imaging-condition editing screen to the display 25 based on the read screen definition information. That is, the input reception unit 26a displays an imaging-condition editing screen for editing imaging conditions included in one of the imaging protocols, selected by the operator, on the display 25.

Figure 4:
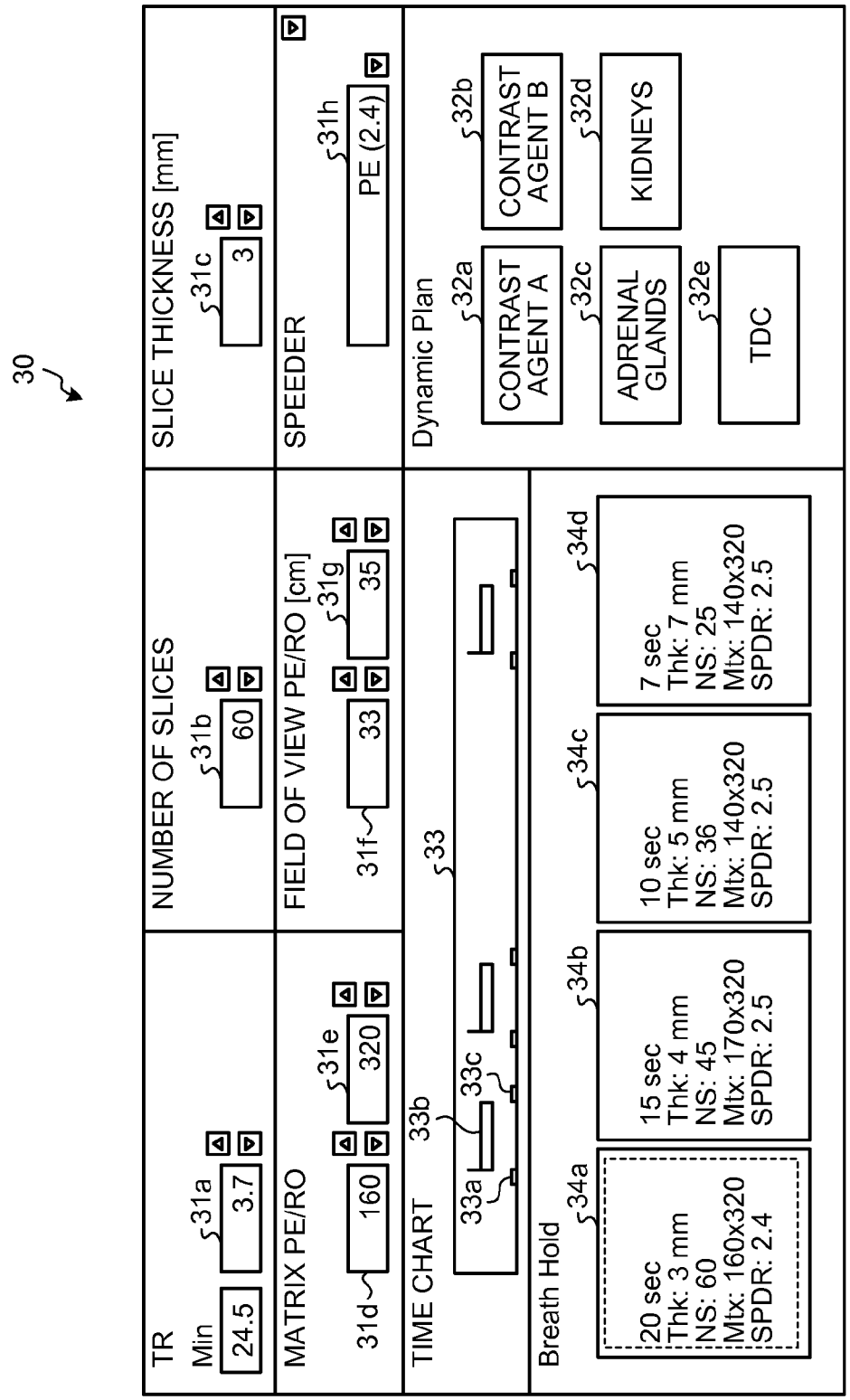
FIG. 4 is an example of an imaging-condition editing screen according to the first embodiment.

FIG. 4 is an example of the imaging-condition editing screen according to the first embodiment. For example, the input reception unit 26a outputs the imaging-condition editing screen 30 shown in FIG. 4 to the display 25. As shown in FIG. 4, a box 31a for inputting the TR, a box 31b for inputting the number of slices, a box 31c for inputting the slice thickness, a box 31d for inputting the PE matrix, a box 31e for inputting the RO matrix, a box 31f for inputting the size of the FOV in the phase encode direction, a box 31g for inputting the size of the FOV in the read out direction, and a box 31h for inputting the SPEEDER ratio are arranged on the imaging-condition editing screen 30, for example.

Buttons 32a, 32b, 32c, 32d, and 32e for selecting types of imaging are also arranged on the imaging-condition editing screen 30. The button 32a is for selecting dynamic imaging using a contrast agent A and the button 32b is for selecting dynamic imaging using a contrast agent B. The button 32c is for selecting dynamic imaging of adrenal glands and the button 32d is for selecting dynamic imaging of kidneys. The button 32e is for selecting imaging to obtain a TDC (Time Density Curve) related to an imaging target region.

A time chart area 33 for displaying a time chart related to a selected type of imaging is also arranged on the imaging-condition editing screen 30. For example, when imaging accompanied by breath hold is selected, a time chart in which sets of three graphics, that is, rectangular graphics 33a, 33b, and 33c arranged in the chronological order, the number of which sets is equal to the number of times of imaging, are placed is displayed in the time chart area 33. In this case, the graphic 33a indicates a timing and a period when a subject is instructed to breathe in, breathe out, and hold the breath. The graphic 33b indicates a timing and a period when imaging is executed. The graphic 33c indicates a timing and a period when the subject is instructed to relax.

Buttons 34a, 34b, 34c, and 34d for selecting values of the breath holdable time are also arranged on the imaging-condition editing screen 30. The button 34a is for selecting 20 seconds as the breath holdable time and the button 34b is for selecting 15 seconds as the breath holdable time. The button 34c is for selecting 10 seconds as the breath holdable time and the button 34d is for selecting 7 seconds as the breath holdable time. Parameter values of the imaging parameters associated with each of the breath holdable times in the setting information that is stored in the breath-hold setting-information storage unit 23c are displayed on the corresponding button. That is, a part of the imaging conditions included in the imaging protocol selected by an operator are displayed on the imaging-condition editing screen 30 with respect to each of the breath holdable times.

For example, when receiving selection of a protocol from the operator after the imaging-condition editing screen 30 is output on the display 25, the input reception unit 26a refers to the preset-information storage unit 23a and reads the preset information corresponding to the selected protocol. The input reception unit 26a displays parameter values of the imaging parameters that are set in the read preset information on the imaging-condition editing screen 30. In the example shown in FIG. 4, the input reception unit 26a displays a value of the TR in the box 31a located on the imaging-condition editing screen 30, a value of the number of slices in the box 31b, a value of the slice thickness in the box 31c, a value of the PE matrix in the box 31d, a value of the RO matrix in the box 31e, a size of the FOV in the phase encode direction in the box 31f, a size of the FOV in the read out direction in the box 31g, and a value of the SPEEDER ratio in the box 31h. The input reception unit 26a then instructs the time-chart-display control unit 26b explained later to display a time chart. Accordingly, a time chart corresponding to the parameter values of the imaging parameters that are displayed on the imaging-condition editing screen 30 is displayed in the time chart area 33.

For example, when an operation of pressing any of the buttons 32a to 32e on the imaging-condition editing screen 30 is performed by the operator, the input reception unit 26a instructs the time-chart-display control unit 26b explained later to display a time chart. This updates display of a time chart in the time chart area 33 according to the parameter values of the imaging parameters displayed on the imaging-condition editing screen 30.

For example, when an operation of pressing any of the buttons 34a to 34d on the imaging-condition editing screen 30 is performed by the operator, that is, when receiving an operation of selecting a part of imaging conditions corresponding to one of the breath holdable times, the input reception unit 26a instructs the parameter adjustment unit 26c explained later to adjust the parameter values. This adjusts the parameter values of the imaging parameters displayed on the imaging-condition editing screen 30 according to the breath holdable time selected by the operator. The input reception unit 26a then instructs the time-chart-display control unit 26b explained later to display a time chart. Accordingly, display of a time chart in the time chart area 33 is updated according to the adjusted parameter values of the imaging parameters.

For example, when receiving an instruction from the operator to determine the imaging conditions, the input reception unit 26a stores the parameter values of the imaging parameters displayed on the imaging-condition editing screen 30 at the time of reception of the instruction in the imaging-condition storage unit 23d.

For example, when receiving an instruction from the operator to start imaging, the input reception unit 26a instructs the imaging-execution control unit 26d to start imaging.

Referring back to FIG. 2, the time-chart-display control unit 26b displays a time chart indicating a timing of execution of imaging accompanied by breath hold of a subject on the display 25. The time-chart-display control unit 26b also changes display of a time chart according to adjustment of the parameter values performed by the parameter adjustment unit 26c.

Specifically, when display of a time chart is instructed by the input reception unit 26a, the time-chart-display control unit 26b calculates a timing and a period when a subject is instructed to breathe, a timing and a period when imaging is executed, and a timing and a period when the subject is instructed to relax using the parameter values displayed on the imaging-condition editing screen 30 at the time of the instruction. The time-chart-display control unit 26b then displays the graphics 33a, 33b, and 33c indicating a time chart in the time chart area 33 based on the calculated timings and periods. Accordingly, each time the display of a time chart is instructed by the input reception unit 26a, a displayed time chart is changed according to the parameter values displayed on the imaging-condition editing screen 30.

The parameter adjustment unit 26c adjusts the parameter values of the imaging parameters included in the imaging conditions for imaging of a subject, according to the breath holdable time received by the input reception unit 26a.

Specifically, when being instructed by the input reception unit 26a to adjust the parameter values, the parameter adjustment unit 26c refers to breath-hold setting information related to the protocol selected by an operator, among the breath-hold setting information stored in the breath-hold setting-information storage unit 23c and obtains the parameter values corresponding to the breath holdable time received by the input reception unit 26a. The parameter adjustment unit 26c then adjusts the parameter values of the imaging parameters included in the imaging conditions using the obtained parameter values.

Figure 5:
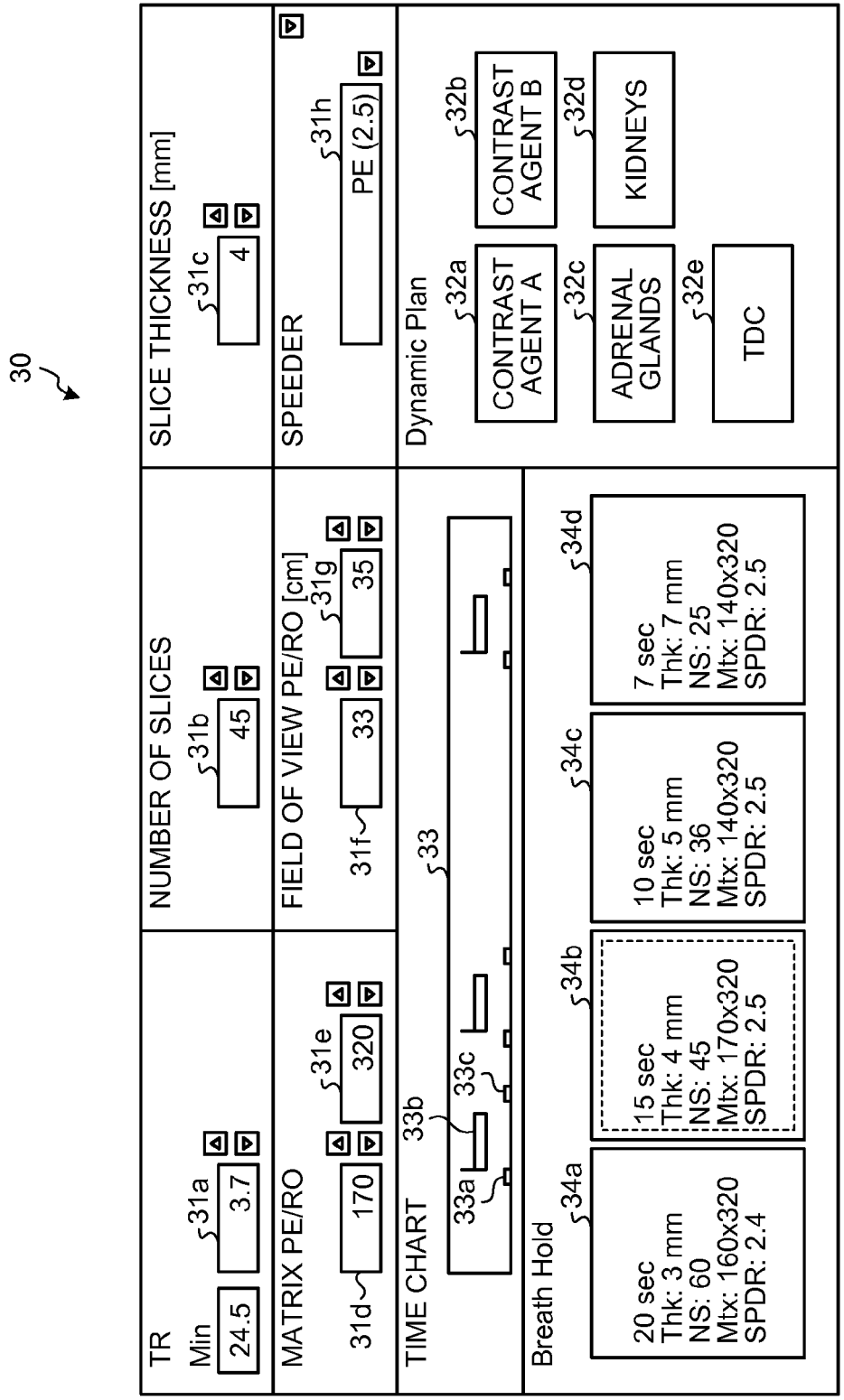
Figure 6:
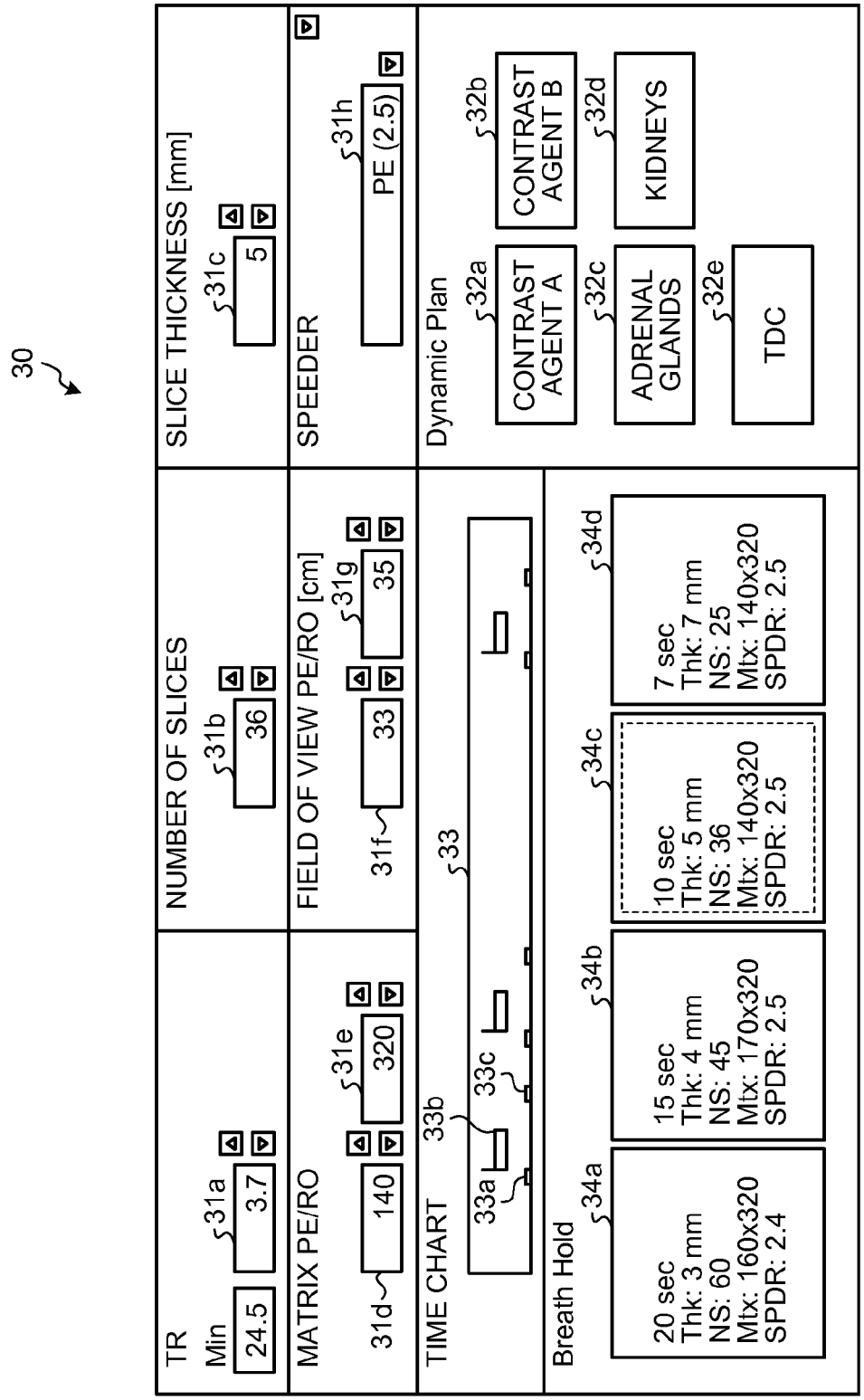

FIGS. 5 to 7 are explanatory diagrams of adjustment of parameter values performed by the parameter adjustment unit 26c according to the first embodiment. A case where the breath-hold setting information shown in FIG. 3 is stored in the breath-hold setting-information storage unit 23c is explained as an example.

For example, when the button 34b is pressed by an operator as shown in FIG. 5, the parameter adjustment unit 26c refers to the breath-hold setting information stored in the breath-hold setting-information storage unit 23c to obtain the slice thickness "0.004 (m)", the number of slices "45", the PE matrix "170", the RO matrix "320", and the SPEEDER ratio "2.5" corresponding to the breath holdable time "15 (seconds)" and displays these parameter values in the corresponding boxes on the imaging-condition editing screen 30.

For example, when the button 34c is pressed by the operator as shown in FIG. 6, the parameter adjustment unit 26c refers to the breath-hold setting information stored in the breath-hold setting-information storage unit 23c to obtain the slice thickness "0.005 (m)", the number of slices "36", the PE matrix "140", the RO matrix "320", and the SPEEDER ratio "2.5" corresponding to the breath holdable time "10 (seconds)" and displays these parameter values in the corresponding boxes on the imaging-condition editing screen 30.

For example, when the button 34d is pressed by the operator as shown in FIG. 7, the parameter adjustment unit 26c refers to the breath-hold setting information stored in the breath-hold setting-information storage unit 23c to obtain the slice thickness "0.007 (m)", the number of slices "25", the PE matrix "140", the RO matrix "320", and the SPEEDER ratio "2.5" corresponding to the breath holdable time "7 (seconds)" and displays these parameters in the corresponding boxes on the imaging-condition editing screen 30.

As mentioned above, when any of the buttons 34a, 34b, 34c, and 34d is pressed by the operator, the parameter adjustment unit 26c is instructed by the input reception unit 26a to adjust the parameter values and also the time-chart-display control unit 26b is instructed to display a time chart. As a result, as shown in FIGS. 5 to 7, each time the parameter adjustment unit 26c adjusts the parameter values of the imaging parameters, time chart display in the time chart area 33 is updated according to the adjusted parameter values of the imaging parameters.

While the case where the parameter adjustment unit 26c adjusts the parameter values based on the breath-hold setting information stored in the breath-hold setting-information storage unit 23c is explained in the present embodiment as an example, the embodiment is not limited thereto. For example, the parameter adjustment unit 26c may calculate the parameter values of the imaging parameters according to the breath holdable time received by the input reception unit 26a based on correlative relations between the breath holdable time and the parameter values of the imaging parameters and may adjust the parameter values of the imaging parameters included in the imaging conditions using the calculated parameter values. In such a case, for example, the parameter adjustment unit 26c defines calculation formulae indicating correlative relations between the respective parameter values of the imaging parameters and the breath holdable time with respect to the imaging parameters and calculates the respective parameter values of the imaging parameters according to the breath holdable time selected by an operator using the defined correlative relations.

Referring back to FIG. 2, the imaging-execution control unit 26d controls imaging according to an instruction from an operator. Specifically, when instructed to start imaging by the input reception unit 26a, the imaging-execution control unit 26d generates sequence information based on the imaging conditions stored in the imaging-condition storage unit 23d and transmits the generated sequence information to the sequence controller 10. The sequence information is transmitted to the sequence controller 10 via the interface 21. Accordingly, scanning of a subject is executed by the sequence controller 10.

The screen-definition editing unit 26e edits the screen definition information stored in the screen-definition storage unit 23b according to an instruction from the operator. Specifically, the screen-definition editing unit 26e receives an operation to register, change, or delete arrangement of the constituent elements such as the labels, the text boxes, and the buttons to be displayed on the imaging-condition editing screen 30, characters displayed on the buttons, relations between the constituent elements and the imaging parameters, and the like from the operator via the input device 24. The screen-definition editing unit 26e then updates contents of the screen definition information stored in the screen-definition storage unit 23b according to the operation received from the operator. Because the screen definition information is stored as an external file as mentioned above, the operator can change a layout of the imaging-condition editing screen 30 by appropriately updating the screen definition information using the screen-definition editing unit 26e, without altering a program for generating the imaging-condition editing screen 30.

The breath-hold setting-information editing unit 26f edits the breath-hold setting information stored in the breath-hold setting-information storage unit 23c according to an instruction from the operator. Specifically, the breath-hold setting-information editing unit 26f receives an operation to register, change, or delete the breath-hold setting information from the operator via the input device 24. The breath-hold setting-information editing unit 26f updates contents of the breath-hold setting information stored in the breath-hold setting-information storage unit 23c according to the operation received from the operator. Because the breath-hold setting information is stored as an external file as mentioned above, the operator can easily change the breath holdable time or the parameter values of the imaging parameters corresponding to the breath holdable time by appropriately updating the breath-hold setting information using the breath-hold setting-information editing unit 26f.

Figure 8:
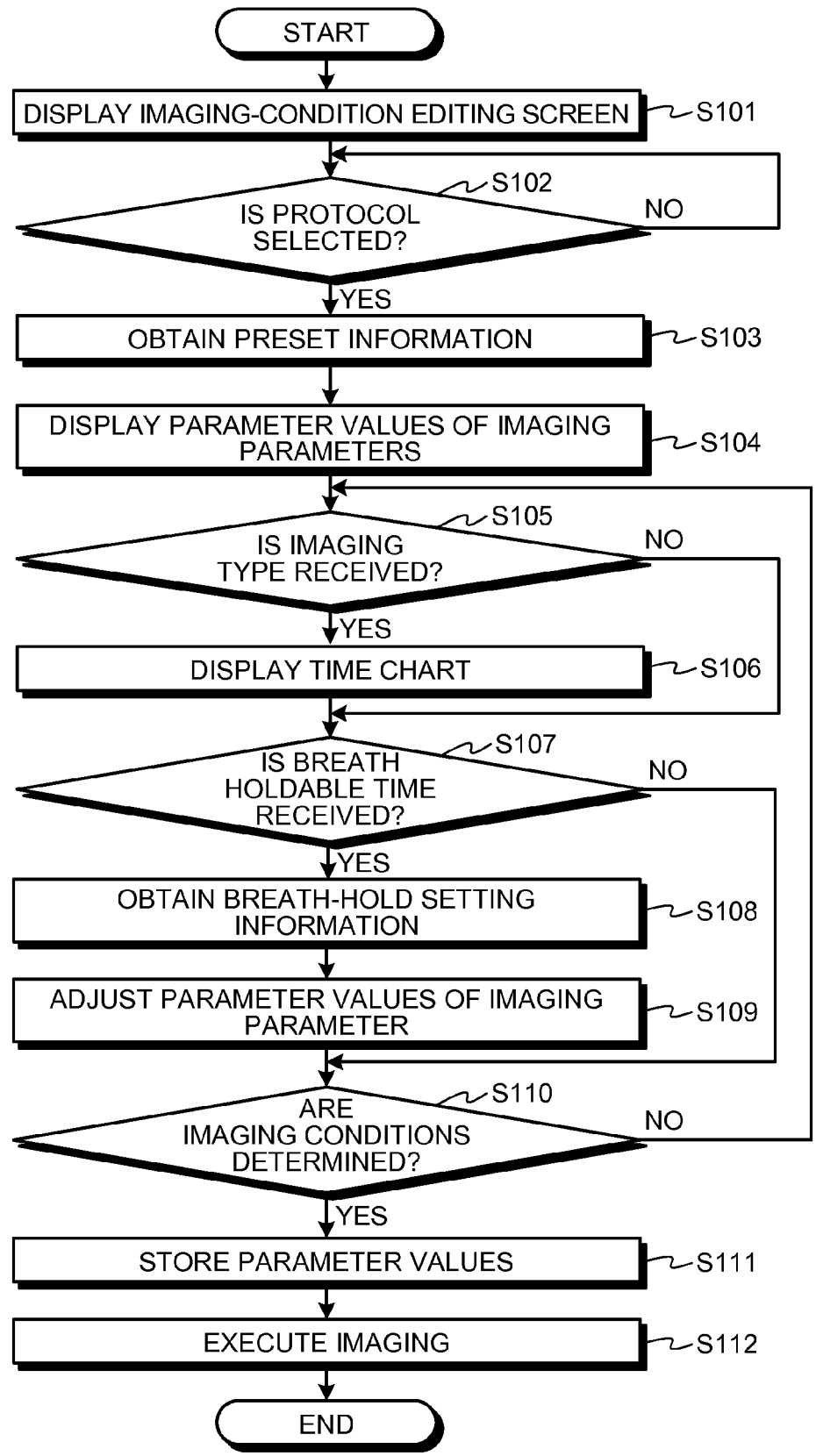
FIG. 8 is a flowchart of an operation of the MRI apparatus according to the first embodiment.

An operation of the MRI apparatus 100 according to the first embodiment is explained next. FIG. 8 is a flowchart of an operation of the MRI apparatus 100 according to the first embodiment. As shown in FIG. 8, in the MRI apparatus 100 according to the first embodiment, when the input reception unit 26a receives a request for display of the imaging-condition editing screen 30 from an operator, the imaging-condition editing screen 30 is displayed on the display 25 (Step S101).

Thereafter, when the operator then selects a protocol (YES at Step S102), the input reception unit 26a refers to the preset-information storage unit 23a and obtains preset information corresponding to the selected protocol (Step S103). The input reception unit 26a then displays parameter values of imaging parameters that are set in the read preset information on the imaging-condition editing screen 30 (Step S104).

Thereafter, when the operator presses any of the buttons 32a to 32e on the imaging-condition editing screen 30 so that the input reception unit 26a receives a type of imaging (YES at Step S105), the time-chart-display control unit 26b displays a time chart corresponding to the type of imaging selected by the operator in the time chart area 33 on the imaging-condition editing screen 30 (Step S106).

Thereafter, when the operator presses any of the buttons 34a to 34d on the imaging-condition editing screen 30 so that the input reception unit 26a receives a breath holdable time (YES at Step S107), the parameter adjustment unit 26c refers to the breath-hold setting-information storage unit 23c and obtains the breath-hold setting information corresponding to the breath holdable time selected by the operator (Step S108). The parameter adjustment unit 26c then adjusts parameter values of imaging parameters included in imaging conditions for imaging of a subject based on the obtained breath-hold setting information (Step S109).

Thereafter, when then receiving an instruction to determine the imaging conditions from the operator (YES at Step S110), the input reception unit 26a stores parameter values of the imaging parameters displayed on the imaging-condition editing screen 30 at the time of reception of the instruction in the imaging-condition storage unit 23d (Step S111). When the input reception unit 26a receives an instruction to start imaging from the operator, the imaging-execution control unit 26d executes imaging based on the imaging conditions stored in the imaging-condition storage unit 23d (Step S112).

As mentioned above, with the MRI apparatus 100 according to the first embodiment, the operator can adjust the imaging parameters according to a simple index of the breath holdable time. Accordingly, the imaging conditions can be appropriately set regardless of special knowledge of the operator. As a result, images with a uniform image quality independent of the operator can be obtained.

Second Embodiment

A second embodiment is explained next. While the case where the parameter values of the imaging parameters are set according to the breath holdable time is explained in the first embodiment, a case where the parameter values of the imaging parameters are set according to a combination of the breath holdable time and an imaging region is explained in the second embodiment. While an MRI apparatus according to the second embodiment includes basically the same configuration as that of the MRI apparatus 100 according to the first embodiment, breath-hold setting information stored in the breath-hold setting-information storage unit 23c and processes performed by the input reception unit 26a and the parameter adjustment unit 26c are mainly different. In the second embodiment, different points from the first embodiment in the breath-hold setting-information storage unit 23c, the input reception unit 26a, the parameter adjustment unit 26c, and the time-chart-display control unit 26b are principally explained.

In the second embodiment, the breath-hold setting-information storage unit 23c stores therein the parameter values of the imaging parameters with respect to each breath holdable time and each imaging region, as breath-hold setting information.

FIG. 9 is an example of breath-hold setting information according to the second embodiment. As shown in FIG. 9, in the second embodiment, the breath-hold setting-information storage unit 23c stores therein information of the imaging region, the breath holdable time (seconds), the slice thickness (m), the number of slices, the PE matrix, the RO matrix, and the SPEEDER ratio associated with each other.

The imaging region can be further divided according to the sizes of the FOV in the body axis direction. For example, as shown in FIG. 9, the liver is further divided into a case (liver 23 cm) where the FOV in the body axis direction is 23 centimeters and a case (liver 18 cm) where the FOV in the body axis direction is 18 centimeters. In some regions of a subject, the size of the FOV in the body axis direction may differ according to a situation of the subject. For example, it is known that the size of the liver in the body axis direction is larger as the subject is slimmer. It is also known that the size of the FOV in the body axis direction affects a relation between the slice thickness and the number of slices. Therefore, when the imaging region is further divided according to the sizes of the FOV in the body axis direction, the parameter values of the imaging parameters can be defined more finely.

In the second embodiment, the input reception unit 26a also receives an imaging region of the subject. When the imaging region is further divided according to the sizes of the FOV in the body axis direction of the subject as shown in FIG. 9, the input reception unit 26a also receives a size of the FOV in the body axis direction of the subject. FIGS. 10 to 14 are examples of an imaging-condition editing screen according to the second embodiment. For example, the input reception unit 26a outputs the imaging-condition editing screens 130 shown in FIGS. 10 to 14 to the display 25.

As shown in FIGS. 10 to 14, for example, the box 31d for inputting the PE matrix, the box 31e for inputting the RO matrix, the box 31b for inputting the number of slices, the box 31c for inputting the slice thickness, and the box 31h for inputting the SPEEDER ratio are arranged on the imaging-condition editing screen 130. The time chart area 33 for displaying a time chart related to a selected type of imaging is also arranged on the imaging-condition editing screen 130.

In the second embodiment, a plurality of tabs defined with respect to imaging regions, respectively, are arranged on the imaging-condition editing screen 130 and buttons for selecting values of the breath holdable time and buttons for selecting types of imaging are arranged on each of the tabs. That is, a part of imaging conditions included in an imaging protocol selected by an operator are displayed on the imaging-condition editing screen 130 with respect to each of combinations of the breath holdable times and the imaging regions. A part of imaging conditions are also displayed on the imaging-condition editing screen 130 with respect to each type of imaging accompanied by breath hold of a subject. When an imaging region is further divided according to the sizes of the FOV in the body axis direction of the subject as shown in FIG. 9, tabs are further divided with respect to each of the imaging regions according to the sizes of the FOV in the body axis direction of the subject. That is, a part of imaging conditions are displayed on the imaging-condition editing screen 130 with respect to each of combinations of the breath holdable times and the sizes of the FOV in the body axis direction of the subject. The operator can select one of the imaging regions or one of the combinations of the imaging regions and the sizes of the FOV in the body axis direction of the subject by selecting one of the tabs.

Figure 10:
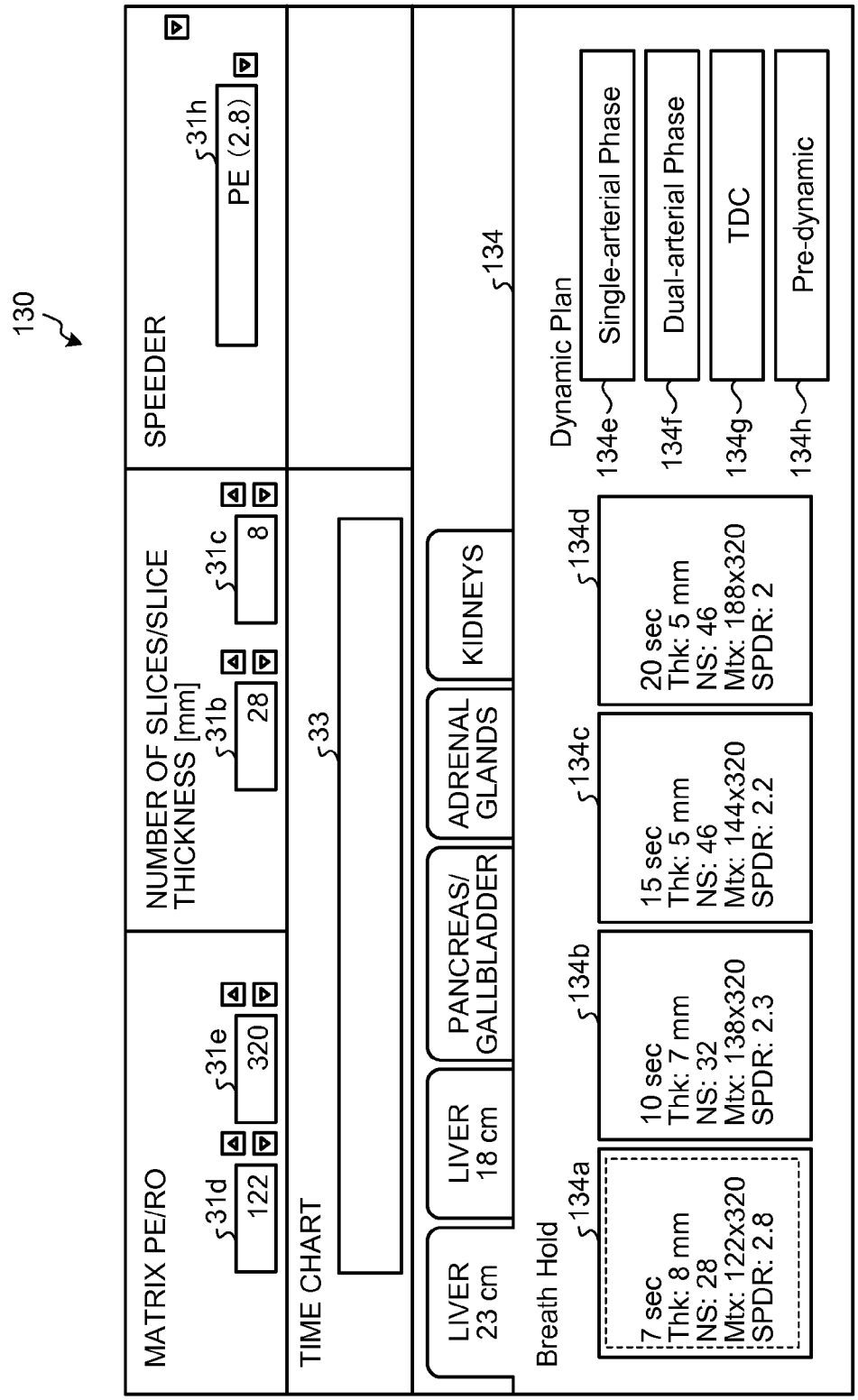
FIGS. 10 to 14 are examples of an imaging-condition editing screen according to the second embodiment.

For example, as shown in FIG. 10, buttons 134a, 134b, 134c, and 134d for selecting values of the breath holdable time are arranged on a tab 134 corresponding to the liver 23 cm (centimeters). The button 134a is for selecting 7 seconds as the breath holdable time and the button 134b is for selecting 10 seconds as the breath holdable time. The button 134c is for selecting 15 seconds as the breath holdable time and the button 134d is for selecting 20 seconds as the breath holdable time. Buttons 134e, 134f, 134g, and 134h for selecting types of imaging are also arranged on the tab 134. The button 134e is for selecting Single-arterial Phase imaging to image three time phases of one arterial phase (a time phase immediately after angiography), one portal-venous phase, and one equilibrium phase. The button 134f is for selecting Dual-arterial Phase imaging to image four time phases of two arterial phases, one portal-venous phase, and one equilibrium phase. The button 134g is for selecting imaging to obtain a TDC of five time phases at regular intervals. The button 134h is for selecting Pre-dynamic imaging to obtain an image at the time of switching off dynamic imaging (an image before angiography).

Figure 11:
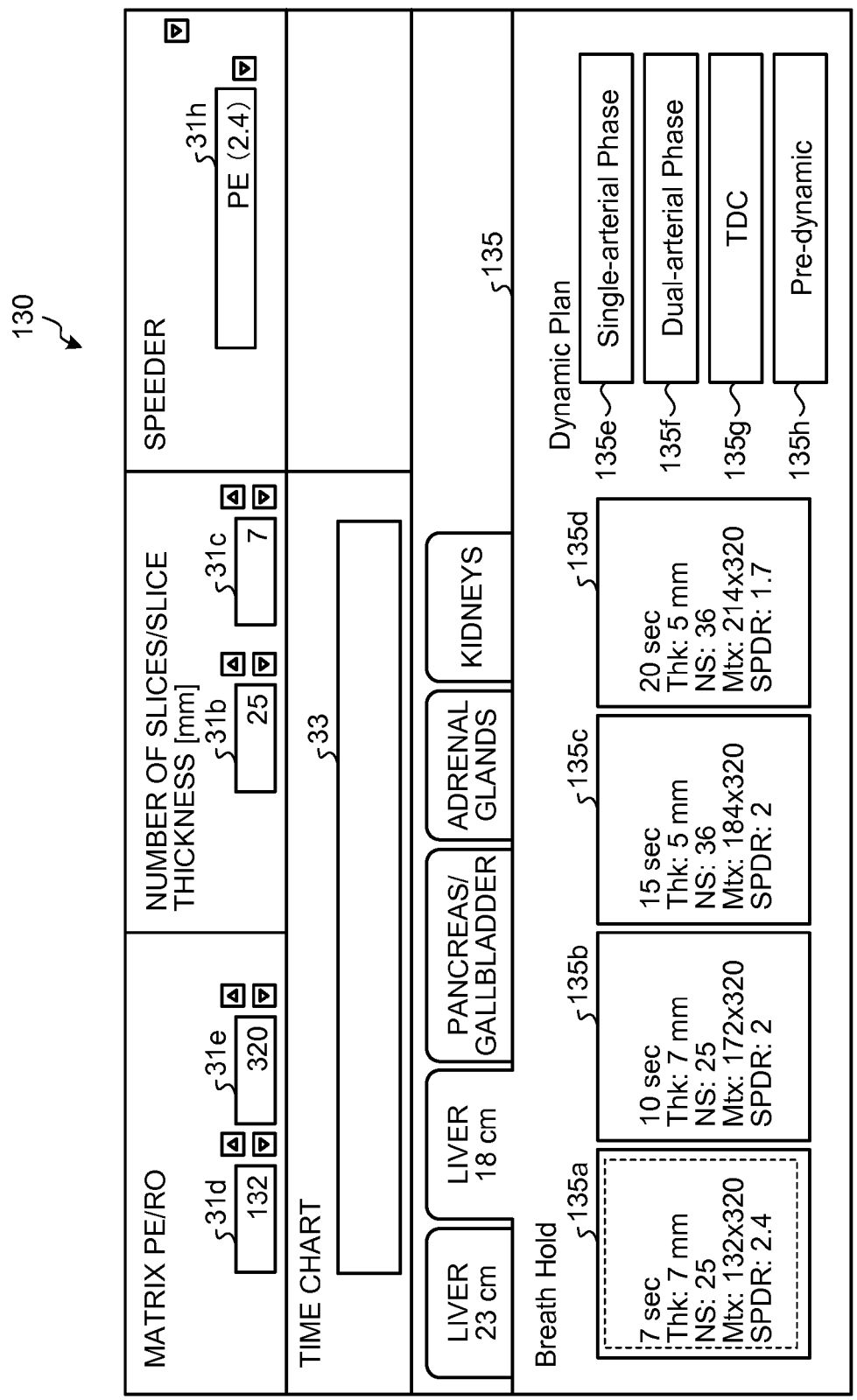

For example, buttons 135a, 135b, 135c, and 135d for selecting values of the breath holdable time are arranged on a tab 135 corresponding to the liver 18 cm (centimeters), as shown in FIG. 11. The button 135a is for selecting 7 seconds as the breath holdable time and the button 135b is for selecting 10 seconds as the breath holdable time. The button 135c is for selecting 15 seconds as the breath holdable time and the button 135d is for selecting 20 seconds as the breath holdable time. Buttons 135e, 135f, 135g, and 135h for selecting types of imaging are also arranged on the tab 135. The button 135e is for selecting the Single-arterial Phase imaging and the button 135f is for selecting the Dual-arterial Phase imaging. The button 135g is for selecting imaging to obtain a TDC and the button 135h is for selecting the Pre-dynamic imaging.

Figure 12:
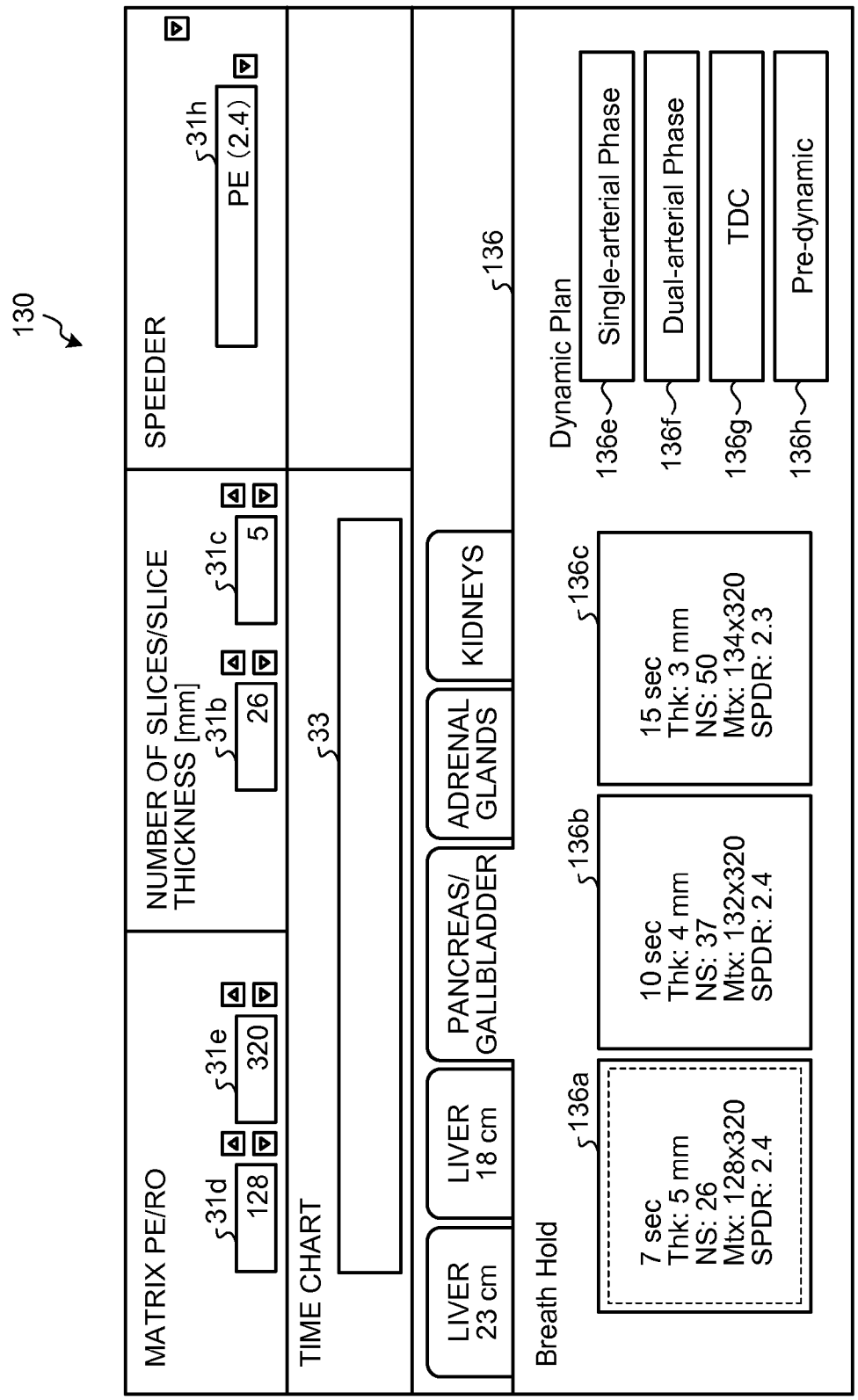

For example, buttons 136a, 136b, and 136c for selecting values of the breath holdable time are arranged on a tab 136 corresponding to the pancreas/gallbladder as shown in FIG. 12. The button 136a is for selecting 7 seconds as the breath holdable time and the button 136b is for selecting 10 seconds as the breath holdable time. The button 136c is for selecting 15 seconds as the breath holdable time. Buttons 136e, 136f, 136g, and 136e for selecting types of imaging are also arranged on the tab 136. The button 136e is for selecting the Single-arterial Phase imaging and the button 136f is for selecting the Dual-arterial Phase imaging. The button 136g is for selecting imaging to obtain a TDC and the button 136h is for selecting the Pre-dynamic imaging.

Figure 13:
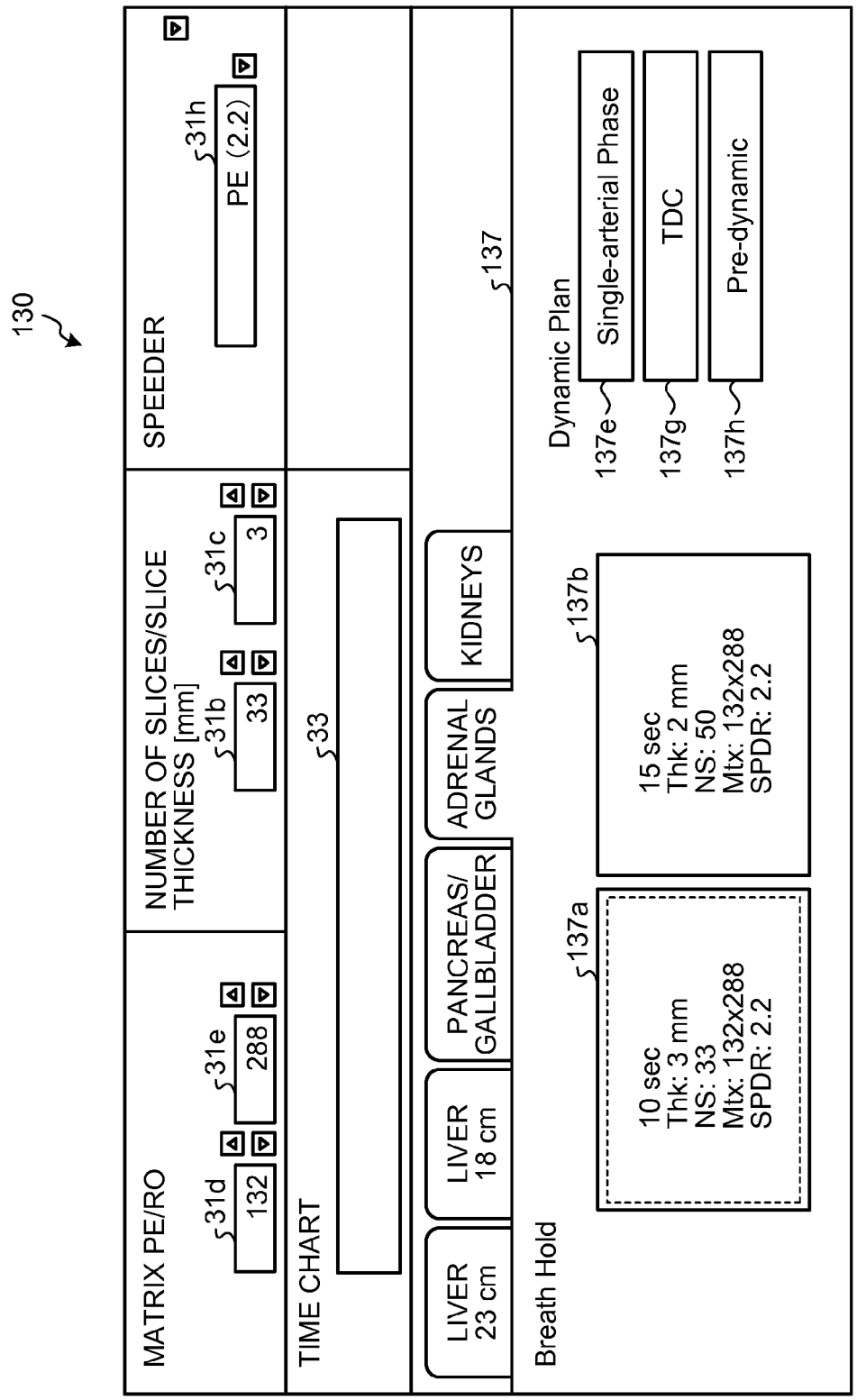

For example, buttons 137a and 137b for selecting values of the breath holdable time are arranged on a tab 137 corresponding to the adrenal glands as shown in FIG. 13. The button 137a is for selecting 10 seconds as the breath holdable time and the button 137b is for selecting 15 seconds as the breath holdable time. Buttons 137e, 137g, and 137h for selecting types of imaging are also arranged on the tab 137. The button 137e is for selecting the Single-arterial Phase imaging and the button 137g is for selecting imaging to obtain a TDC. The button 137h is for selecting the Pre-dynamic imaging.

Figure 14:
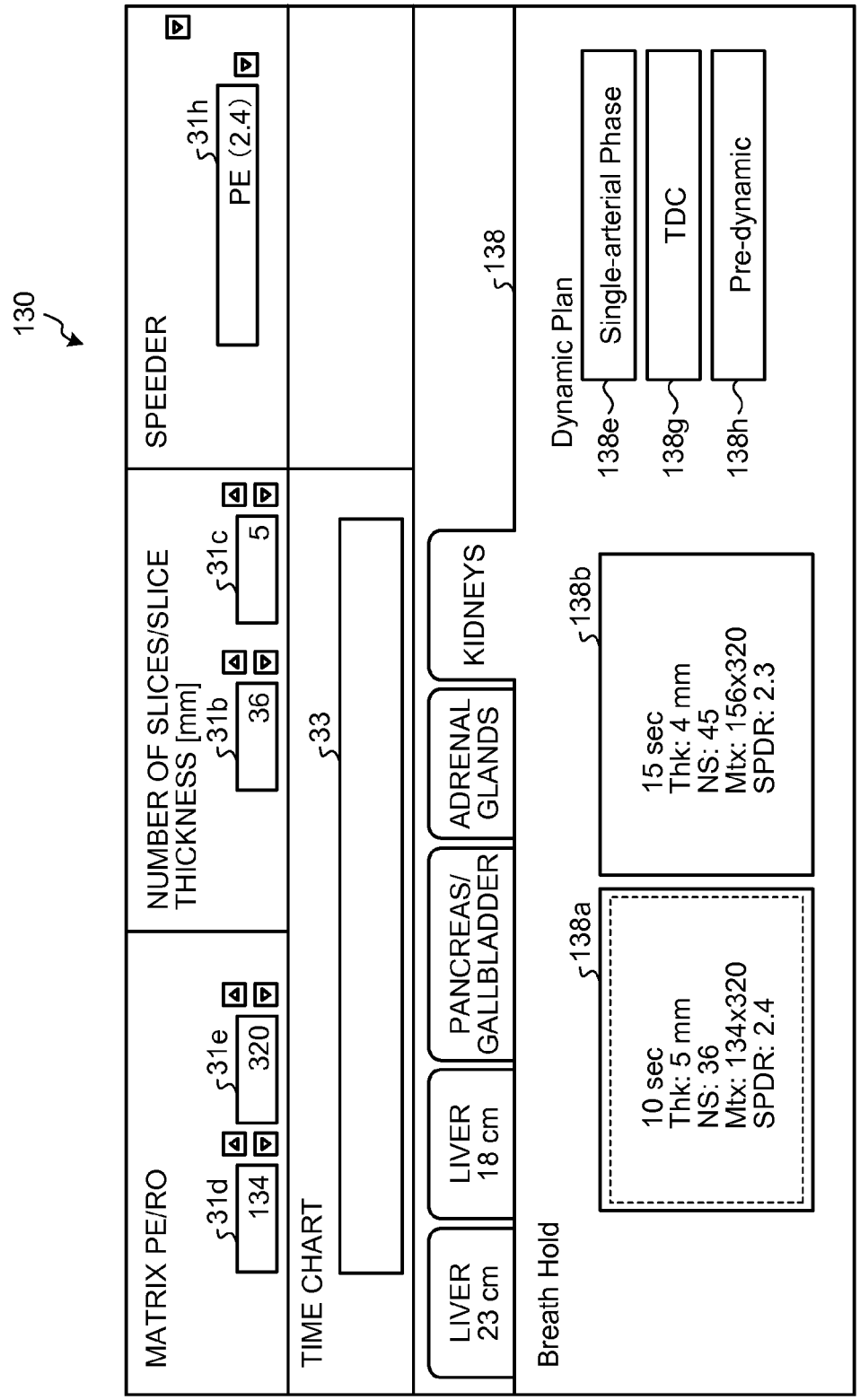

For example, buttons 138a and 138b for selecting values of the breath holdable time are arranged on a tab 138 corresponding to the kidneys as shown in FIG. 14. The button 138a is for selecting 10 seconds as the breath holdable time and the button 138b is for selecting 15 seconds as the breath holdable time. Buttons 138e, 138g, and 138h for selecting types of imaging are also arranged on the tab 138. The button 138e is for selecting the Single-arterial Phase imaging and the button 138g is for selecting imaging to obtain a TDC. The button 138h is for selecting the Pre-dynamic imaging.

As described above, in the second embodiment, an operator can select a combination of the breath holdable time and the imaging region by selecting any of the tabs on the imaging-condition editing screen 130 and further selecting any of the buttons for selecting values of the breath holdable time arranged on the corresponding tab.

In the second embodiment, the parameter adjustment unit 26c adjusts parameter values of imaging parameters included in imaging conditions for imaging of a subject according to a combination of the breath holdable time and the imaging region received by the input reception unit 26a. That is, the input reception unit 26a receives an operation to select a part of imaging conditions corresponding to a plurality of combinations of the breath holdable times and the imaging regions. The input reception unit 26a also receives an operation to select a part of imaging conditions corresponding to a combination of the breath holdable time and the size of the FOV in the body axis direction of the subject. The input reception unit 26a also receives an operation to select a part of imaging conditions corresponding to a type of imaging. A case where the breath-hold setting information shown in FIG. 9 is stored in the breath-hold setting-information storage unit 23c is explained as an example.

For example, it is assumed, in a state where the tab 135 corresponding to the liver 18 cm is displayed as shown in FIG. 11, the button 135a among the buttons 135a, 135b, 135c, and 135d that are arranged on the tab 135 is pressed by an operator. In such a case, the parameter adjustment unit 26c refers to the breath-hold setting information stored in the breath-hold setting-information storage unit 23c to obtain the slice thickness "0.007 (m)", the number of slices "25", the PE matrix "132", the RO matrix "320", and the SPEEDER ratio "2.4" corresponding to the imaging region "the liver 18 cm" and the breath holdable time "7 (seconds)" and displays the parameter values in the corresponding boxes on the imaging-condition editing screen 130.

For example, it is assumed, in a state where the tab 136 corresponding to the pancreas/gallbladder is displayed as shown in FIG. 12, the button 136a among the buttons 136a, 136b, and 136c that are arranged on the tab 136 is pressed by an operator. In such a case, the parameter adjustment unit 26c refers to the breath-hold setting information stored in the breath-hold setting-information storage unit 23c to obtain the slice thickness "0.005 (m)", the number of slices "26", the PE matrix "128", the RO matrix "320", and the SPEEDER ratio "2.4" corresponding to the imaging region "pancreas/gallbladder" and the breath holdable time "7 (seconds)" and displays the parameter values in the corresponding boxes on the imaging-condition editing screen 130.

For example, it is assumed, in a state where the tab 137 corresponding to the adrenal glands is displayed as shown in FIG. 13, the button 137a out of the buttons 137a and 137b that are arranged on the tab 137 is pressed by an operator. In such a case, the parameter adjustment unit 26c refers to the breath-hold setting information stored in the breath-hold setting-information storage unit 23c to obtain the slice thickness "0.003 (m)", the number of slices "33", the PE matrix "132", the RO matrix "288", and the SPEEDER ratio "2.2" corresponding to the imaging region "adrenal glands" and the breath holdable time "10 (seconds)" and displays the parameter values in the corresponding boxes on the imaging-condition editing screen 130.

For example, it is assumed, in a state where the tab 138 corresponding to the kidneys is displayed as shown in FIG. 14, the button 138a out of the buttons 138a and 138b that are arranged on the tab 138 is pressed by an operator. In such a case, the parameter adjustment unit 26c refers to the breath-hold setting information stored in the breath-hold setting-information storage unit 23c to obtain the slice thickness "0.005 (m)", the number of slices "36", the PE matrix "134", the RO matrix "320", and the SPEEDER ratio "2.4" corresponding to the imaging region "kidneys" and the breath holdable time "10 (seconds)" and displays the parameter values in the corresponding boxes on the imaging-condition editing screen 130.

In the second embodiment, the time-chart-display control unit 26b displays a time chart on the display 25 according to a combination of the breath holdable time and the imaging region received by the input reception unit 26a.

FIGS. 15 to 17 are explanatory diagrams of time chart display performed by the time-chart-display control unit 26b according to the second embodiment. Cases where the buttons 135e, 135f, 135g, and 135h for selecting the types of imaging are selected on the tab 135 corresponding to the liver 18 cm are explained as an example.

For example, it is assumed, in a state where the tab 135 corresponding to the liver 18 cm is displayed as shown in FIG. 15, the button 135e among the buttons 135e, 135f, 135g, and 135h that are arranged on the tab 135 is pressed by an operator. In such a case, the time-chart-display control unit 26b displays the graphics 33b indicating timings and periods when imaging is to be executed at positions corresponding to three time phases of one arterial phase, one portal-venous phase, and one equilibrium phase on the time chart based on the parameter values displayed at the time of pressing the button 135e on the imaging-condition editing screen 130.

For example, it is assumed, in a state where the tab 135 corresponding to the liver 18 cm is displayed as shown in FIG. 16, the button 135f among the buttons 135e, 135f, 135g, and 135h that are arranged on the tab 135 is pressed by an operator. In such a case, the time-chart-display control unit 26b displays the graphics 33b indicating timings and periods when imaging is to be executed at positions corresponding to two arterial phases, one portal-venous phase, and one equilibrium phase on the time chart based on the parameter values displayed at the time of pressing the button 135f on the imaging-condition editing screen 130.

For example, it is assumed, in a state where the tab 135 corresponding to the liver 18 cm is displayed as shown in FIG. 17, the button 135g among the buttons 135e, 135f, 135g, and 135h that are arranged on the tab 135 is pressed by an operator. In such a case, the time-chart-display control unit 26b displays the graphics 33b indicating timings and periods when imaging is to be executed at positions corresponding to five time phases at equal intervals on the time chart based on the parameter values displayed at the time of pressing the button 135g on the imaging-condition editing screen 130.

In this way, according to the second embodiment, time chart display changes according to a combination of the breath holdable time and the imaging region upon selection by an operator of any of the tabs and then selection of any of the buttons for selecting the types of imaging arranged on the corresponding tab.

As mentioned above, with the MRI apparatus 100 according to the second embodiment, the operator can adjust the imaging parameters according to simple indexes of the breath holdable time and the imaging region. Accordingly, the imaging conditions can be appropriately set regardless of special knowledge of the operator. As a result, images with a uniform image quality independent of the operator can be obtained.

According to at least one of the embodiments explained above, imaging conditions can be appropriately set regardless of special knowledge of an operator.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging (MRI) apparatus comprising:

MRI system components including static and gradient magnetic field generators, at least one radio frequency (RF) coil, RF transmitter and receiver circuits and an MRI pulse sequence controller coupled to control said MRI system components and including at least one processor coupled to digital memory and to an operator visual display and input interface, said at least one processor being configured to:

pre-store plural sets of MRI pulse sequence parameter values, each set being configured for use with a different non-zero breath hold time;

simultaneously display to an operator a plurality of buttons, each button displaying a different one of the non-zero breath hold times together with display of at least part of its set of said pre stored MRI pulse sequence parameter values including at least one of (a) a slice thickness, (b) a number of slices to be imaged, (c) a number of matrices to be used in the phase encode direction, (d) a number of matrices to be used in the read-out direction, and (e) an acceleration factor of parallel imaging to be used;

receive operator selection of one of the displayed buttons to select a corresponding one of the non-zero breath hold times for a subject to be imaged;

set MRI pulse sequence parameter values in accordance with said operator selection including replacing previously pre-set values for MRI pulse sequence parameter values with the pre-stored MRI pulse sequence parameter values for the selected non-zero breath hold time; and perform an MRI pulse sequence according to the set MRI pulse sequence parameter values.

2. The magnetic resonance imaging apparatus according to claim 1, wherein said at least one processor is further configured to:

receive an operator input identifying an imaging region of the subject, and, set the MRI pulse sequence parameters to be used according to a combination of the operator-set breath hold time and the operator set imaging region.

3. The magnetic resonance imaging apparatus according to claim 2, wherein said at least one processor is further configured to:

receive an operator input representing a size of a field of view of the subject in a body axis direction thereof, and, set the MRI pulse sequence parameters to be used according to a combination of the operator set: (a) breath hold time, (b) the imaging region, and (c) the size of the field of view in the body axis direction.

4. The magnetic resonance imaging apparatus according to claim 1, wherein said at least one processor is further configured to:

store as part of the plural sets of MRI pulse sequence parameter values respectively corresponding to plural different non-zero breath hold times, MRI pulse sequence parameter values including number of matrixes in a phase encode direction, number of matrixes in a readout direction, and acceleration factor of parallel imaging.

5. The magnetic resonance imaging apparatus according to claim 1, wherein said at least one processor is further configured to:

display a time chart indicating execution timing of the set MRI pulse sequence including the timing of breath hold(s) of a subject; and change display of the time chart according to displayed MRI pulse sequence parameter values.

6. The magnetic resonance imaging apparatus according to claim 1, wherein said at least one processor is further configured to receive operator input editing of the stored MRI pulse sequence parameter values.

7. The magnetic resonance imaging apparatus according to claim 1, wherein said at least one processor is further configured to:

store as part of the plural sets of MRI pulse sequence parameter values respectively corresponding to plural different non-zero breath hold times, MRI pulse sequence parameter values including at least one of slice thickness, number of slices, number of matrixes in a phase encode direction, number of matrixes in a readout direction, and acceleration factor of parallel imaging.

8. The magnetic resonance imaging apparatus according to claim 1, wherein said at least one processor is further configured to:
store as part of the plural sets of MRI pulse sequence parameter values respectively corresponding to plural different non-zero breath hold times, MRI pulse sequence parameter values including slice thickness, number of slices, number of matrixes in a phase encode direction, number of matrixes in a readout direction, and acceleration factor of parallel imaging.

9. The magnetic resonance imaging apparatus according to claim 1, wherein said at least one processor is further configured to:
store as part of the plural sets of MRI pulse sequence parameter values respectively corresponding to plural different non-zero breath hold times, MRI pulse sequence parameter values relating to a time required for imaging.

10. The magnetic resonance imaging apparatus according to claim 1, wherein:
the stored plural sets of MRI pulse sequence parameter values respectively corresponding to plural different non-zero breath hold times are based on predetermined relationships between plural MRI pulse sequence parameter values to be used in each one of plural types of imaging sequences displayed to an operator for selection.

11. The magnetic resonance imaging apparatus according to claim 1, wherein:
said stored plural sets of MRI pulse sequence parameter values respectively corresponding to plural different non-zero breath hold times are predetermined based on signal to noise ratio or resolution.

12. A magnetic resonance imaging apparatus (MRI) comprising:
MRI system components including static and gradient magnetic field generators, at least one radio frequency (RF) coil, RF transmitter and receiver circuits and an MRI pulse sequence controller coupled to control said MRI system components and including at least one processor coupled to digital memory and to an operator visual display and input interface, said at least one processor being configured to:
pre-store plural sets of MRI pulse sequence parameter values, each set being configured for use with a different non-zero breath hold time, the MRI pulse sequence parameter values relating to a time required for imaging, and including slice thickness, number of slices, number of matrixes in a phase encode direction, and number of matrixes in a readout direction;
simultaneously display a plurality of buttons to an operator, each button displaying a different one of the non-zero breath hold times together with display of at least part of its set of said pre-stored MRI pulse sequence parameter values including at least one of (a) a slice thickness, (b) a number of slices to be imaged, (c) a number of matrices to be used in the phase encode direction, (d) a number of matrices to be used in the read-out direction, and (e) an acceleration factor of parallel imaging to be used;
receive operator selection of one of the displayed buttons to select a corresponding one of the non-zero breath hold times for a subject to be imaged;
set MRI pulse sequence parameter values in accordance with said operator selection including replacing previously pre-set values for MRI pulse sequence parameter values with the pre-stored MRI pulse sequence parameter values for the selected non-zero breath hold time; and
perform an MRI pulse sequence according to the set MRI pulse sequence parameter values.

13. A magnetic resonance imaging (MRI) method comprising:
using and interacting with an MRI system to effect:
pre-storing plural sets of MRI pulse sequence parameter values, each set being configured for use with a different non-zero breath hold time;
simultaneously displaying to an operator a plurality of buttons, each button displaying a different one of the non-zero breath hold times together with display of at least part of its set of said pre-stored MRI pulse sequence parameter values including at least one of (a) a slice thickness, (b) a number of slices to be imaged, (c) a number of matrices to be used in the phase encode direction, (d) a number of matrices to be used in the read-out direction, and (e) an acceleration factor of parallel imaging to be used;
selecting one of the displayed non-zero breath hold times for a subject to be imaged;
setting MRI pulse sequence parameter values in accordance with said selection including replacing previously pre-set values for MRI pulse sequence parameter values with the pre-stored MRI pulse sequence parameter values for the selected non-zero breath hold time; and
performing an MRI pulse sequence according to the set MRI pulse sequence parameter values.

* * * * *